US005938650A

United States Patent [19]

Baer et al.

[11] Patent Number: 5,938,650

[45] **Date of Patent: *Aug. 17, 1999**

[54] ABSORBENT CORE FOR ABSORBING BODY LIQUIDS AND METHOD

[75] Inventors: Samuel C. Baer, Woodbury, N.J.; Brian E. Boehmer, Philadelphia, Pa.; Kenneth Bononcini, Newfield, N.J.

[73] Assignee: FiberTech Group, Inc., Landisville, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/681,665

[22] Filed: Jul. 29, 1996

Related U.S. Application Data

[63] Continuation-in-part of application No. 08/512,968, Aug. 9, 1995, abandoned.

[51] Int. Cl.[6] .......... A61F 13/15

[52] U.S. Cl. .......... 604/368; 604/378

[58] Field of Search .......... 604/358, 366, 604/368, 372, 370, 378–380, 385.1

[56] References Cited

U.S. PATENT DOCUMENTS

| | | | |
|---|---|---|---|
| 4,055,180 | 10/1977 | Karami | 604/368 |
| 5,401,266 | 3/1995 | Rouneman et al. | 604/383 |
| 5,425,725 | 6/1995 | Tanzer et al. | 604/368 |
| 5,556,393 | 9/1996 | Rönnberg | 604/383 |
| 5,593,399 | 1/1997 | Tanzer et al. | 604/368 |
| 5,601,542 | 2/1997 | Melius et al. | 604/368 |

*Primary Examiner*—Robert A. Clarke

*Attorney, Agent, or Firm*—Juettner Pyle Piontek & Underwood

[57] ABSTRACT

The disclosure describes an absorbent core, free of wood pulp or other cellulosic materials. The core includes two thin outer layers, with at least one layer being porous and receptive to body liquids. A quantity of superabsorbent polymer particles of a particular type is provided between the outer layers and is loosely contained in individual unbonded open zones or flat closed pockets defined by a plurality of intersecting heat bond lines between the layers, with the lines defining a densified and a hot calendar-bonded fiber structure to provided wicking lines or flow zones between the pockets. The dry product is a flat, thin partial laminate.

6 Claims, 2 Drawing Sheets

ABSORBENT CORE FOR ABSORBING BODY LIQUIDS AND METHOD

CROSS-REFERENCE

This is a continuation-in-part application of application Ser. No. 08/512,968, filed Aug. 9, 1995 now abandoned.

BACKGROUND OF THE INVENTION

This invention relates to an absorbent core for absorbing liquids, such as a component of a diaper or incontinent device worn against the body.

Various designs of absorbent cores have been proposed. The absorbent material most normally used are comprised of a blend of cellulose pulp fibers and superabsorbent polymer particles covered by a nonwoven fabric. The pulp content of the core is typically 60–80 per cent of the total core weight.

The use of cellulose pulp has several disadvantages such as: a higher cost per amount of body fluid absorbed than superabsorbing polymer or "SAP" particles; slow fluid acquisition rate when the pulp fiber is compressed to form a compact absorbent article; and the high capital, productivity, and utility cost of operating a pulp mill on each and every absorbent product converting line.

The use of superabsorbent polymer in a pulp-filled core is standard throughout the absorbent product industry. These polymers swell and form a gel when contacted with aqueous liquids and are capable of acquiring and retaining under pressure many times their weight of liquid. The polymers, in powdered form, are typically disposed among pulp fibers in products such as diapers or between layers of nonwoven in products such as absorbent mats.

Since SAP particles are more cost effective than pulp fibers for retaining liquids, the primary role of pulp fibers in absorbent products has evolved from fluid retention to holding the SAP particles in place and to wicking fluid to the SAP particles. The intimate blend of SAP and pulp means that swelling SAP particles engulf the microscopic fluid wicking channels between pulp fibers. This phenomena, called "gel-blocking", prevents fluid from being wicked to many unsaturated areas of the core. Thus, only a fraction of the absorbent core absorbs fluid in use.

Various problems with the use of superabsorbing polymers in absorbent cores and some proposed solutions are described in U.S. Pat. No. 5,013,309. For example, proposals have been made to retain the polymer particles in a fixed position in a fibrous substrate to prevent migration or clumping of the particles.

Proposals have been advanced to use water soluble adhesives in a structure to prevent migration of the SAP polymer. These adhesive, however, add to the cost and processing of the product and reduce flexibility and initial porosity.

In U.S. Pat. No. 5,411,497, pockets of SAP are held between two layers secured together with a water soluble adhesive. When the core becomes wet, the bonded layers come apart, exposing additional SAP and allowing flow between layers.

Another example of an absorbent article containing SAP particles is found in U.S. Pat. No. 4,055,180, which discloses SAP disposed with a bubble film structure to prevent migration, in combination with layers of pulp. Since the plastic bubbles are relatively nonextensible. The pockets cannot swell, and the overall bulk in dry form is very large.

EP 297411 discloses a core filled with thermoplastic fibers and SAP and wrapped in tissue paper. The thermoplastic fibers are also employed to allow sealing by heat fusion, but the bulk due to the fibers is very high, and gel blockage is likely to occur.

SUMMARY OF THE INVENTION

In accordance with the present invention, an absorbent core, free of wood pulp or other cellulosic materials is provided. The core comprises two thin outer layers, with at least one layer being porous and receptive to body liquids. A quantity of superabsorbent polymer particles of a particular type is provided between the outer layers and is loosely contained in individual unbonded open zones or flat closed pockets defined by a plurality of intersecting heat bond lines between the layers, with the lines defining a densified and a hot calendar-bonded fiber structure to provide wicking lines or flow zones between the pockets. The dry product is a flat, thin partial laminate.

The absorbent core or sheet may be made by providing a thermoplastic film or nonwoven fabric, applying superabsorbing polymer powder to the surface at the film or fabric, applying a second nonwoven fabric over the first, and passing the laminate through the nip of a pair of heated rolls, with one of the rolls being engraved to apply a permanent gridwork bonding pattern of spaced interconnected lines between the top and bottom containment layers. The superabsorbing polymer is loosely contained in the flat pockets defined by the bonding gridwork.

When a liquid is applied to one area of the laminate, the polymer particles within the pockets swell, while the bonded lines normally remain intact, resulting in a three dimensional spaced bubble-like structure. As the SAP particles swell, the bonded areas of densified fibers form three dimensional flow channels and allow excess liquid in one location to flow quickly to adjacent and more remote pockets and beyond for additional absorption. This allows for a rate and a total level of liquid absorption which is much higher than conventional products of this nature. In some cases, the pressure caused by the swelling SAP particles can cause rupture of bond lines around one or more pockets, thereby increasing available volume and flow into adjacent, less saturated pockets. Also, the core in its dry state is extremely thin and flexible in comparison to other types of cores with a comparable liquid capacity.

The superabsorbing polymer employed is preferably one that does not form a continuous gel but forms individual swollen particles within each pocket, with the particles remaining mobile and preventing any gel blockage.

DESCRIPTION OF THE PREFERRED EMBODIMENTS

Figure 1:
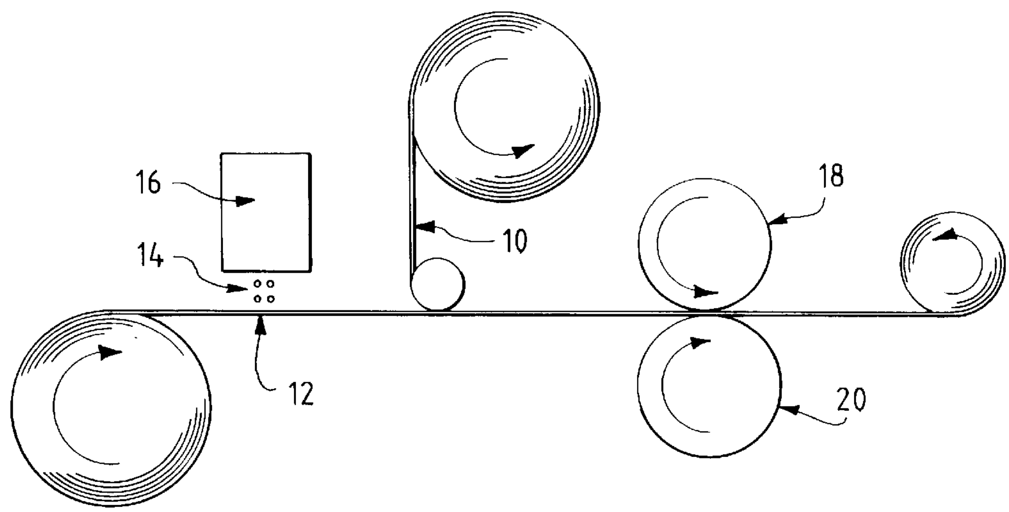
FIG. 1 is a schematic side view illustrating the formation of the absorbent core of the present invention.

The absorbent core of the present invention consists essentially of a pair of flat outer thin sheets 10 and 12 and a quantity of superabsorbing polymer particles or SAP 14 which is heat and pressure laminated between the outer sheets in a particular manner. No cellulosic materials such as pulp or tissue are employed.

At least one of the layers is a nonwoven fabric made from thermoplastic fibers or filaments. Shape retaining nonwoven fabrics are well known and are made by a variety of processes from fibers of polyolefins and polyesters. The fibers used are incapable of absorbing liquids but may be treated with a surfactant for improved wetability. The fabric should be sufficiently porous to allow rapid passage of liquid while sufficiently fine to retain the SAP particles in a dry state. An example of one suitable fabric is a heat bonded or point bonded nonwoven having a basis weight of 18 to 40 grams per square meter and comprising staple polypropylene fibers having a denier of from about 1.2 to about 3.0. An acceptable substitute is a liquid permeable film.

The nonwoven fabric of the porous layer may be provided in a variety of forms. For example, the fabric may be composed solely of heat bondable fibers or may also contain other types of fibers in addition to heat bondable fibers. Also, the nonwoven web may be consolidated by other techniques such as by adhesive bonding or entanglement of fibers, as long as the two layers 10 and 12 can be bonded together.

The porous layer is considered herein as the upper layer, or the layer which faces the body of the user; or is exposed to liquid. The other outer layer may comprise a nonwoven web identical or similar to that described above. If the second layer is intended to be the outermost layer, then it may comprise a nonporous continuous film, or a nonwoven fabric laminated to an outwardly facing film.

The term "superabsorbing polymer" or "SAP" as used herein is a hydrocolloid material which is capable of absorbing many times its own weight of aqueous liquid. These materials are generally prepared by polymerizing one or more monomers, which if homopolymerized by conventional methods, would form water soluble polymers. To render them water insoluble, these polymers or mixtures of them are reacted, usually with a crosslinking agent, or by chain entanglement. The preferred type of SAP is one in which does not form a continuous gel but forms swollen individual particles which are flowable. Known polymers of this type are based on cross linked salts of polyacrylic acid or methacrylic acid, such as the sodium salt of poly-2-properoic acid, available from Micro-Set, Landisville, N.J. Another source is Favor SX FAM sold by Stockhausen in Greensboro, N.C. In the dry state the SAP powder has a particle size in the order of about 100–800 microns. SAP in fiber form may also be employed, and the term "particles" will be deemed to include powders and fibers.

Other optional known powdered materials may be mixed with the SAP powder, such as powdered materials to mask or control odors or to kill bacteria. Otherwise, the pockets are preferably free of other materials such as polymer or natural fibers which tend to increase bulk.

As shown in FIG. 1, the lower web of preformed fabric, film or composite 12 is moved in the direction shown by the arrow, and a quantity of SAP 14 is uniformly deposited on the lower layer 12 by a powder meter 16 or other suitable applicator. The rate of application is preferably in the order of from about 45 to 250 grams per square meter of fabric.

The top porous layer of fabric 10 is then applied, and then the layers are united and passed through the nip of a pair of rolls 18 and 20 under heat and pressure. The surface of one of the rolls is engraved and has a relatively raised repeating bonding pattern. The roll causes portions or lines in the two webs to be compacted with the fibers of the two webs being thermally bonded to form a partial laminate, with the remaining areas being unbonded and have the SAP particles loosely resident therein.

Figure 2:
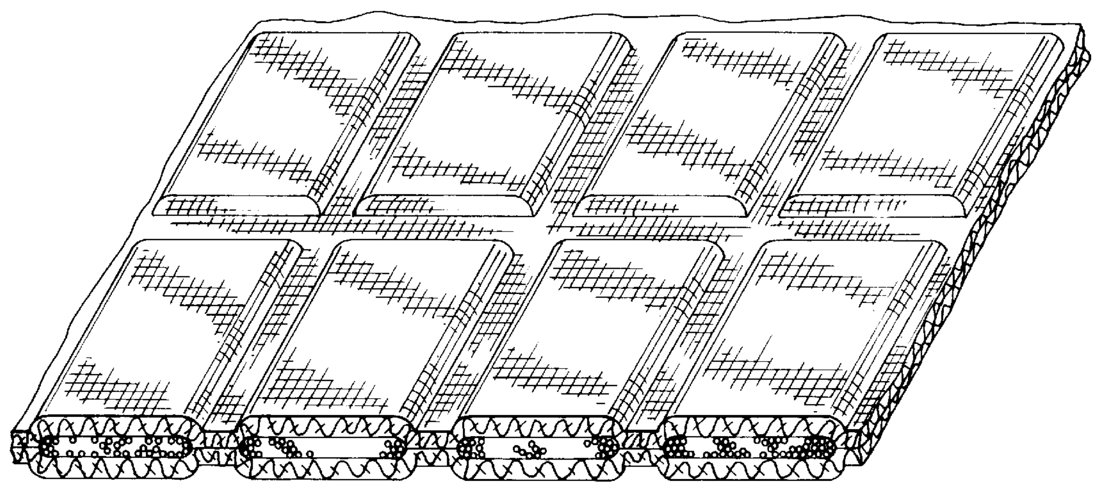
FIG. 2 is a perspective sectional view of the core of the present invention in a dry state.
Figure 5:
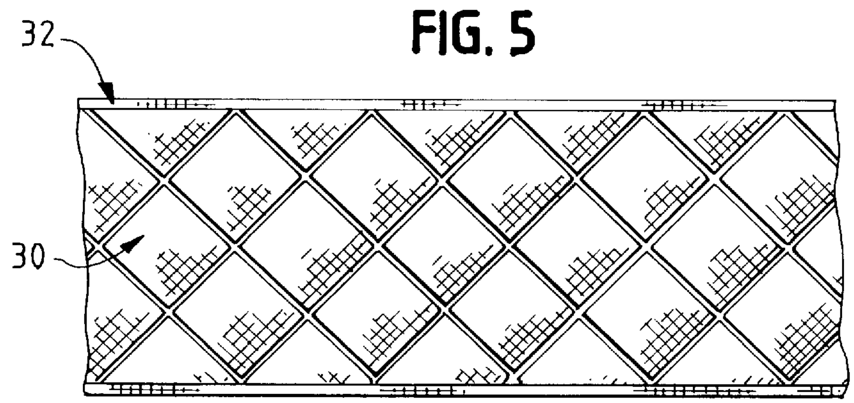
FIG. 5 is a first top view of the absorbent core of the present invention, together with additional optional layers.
Figure 6:
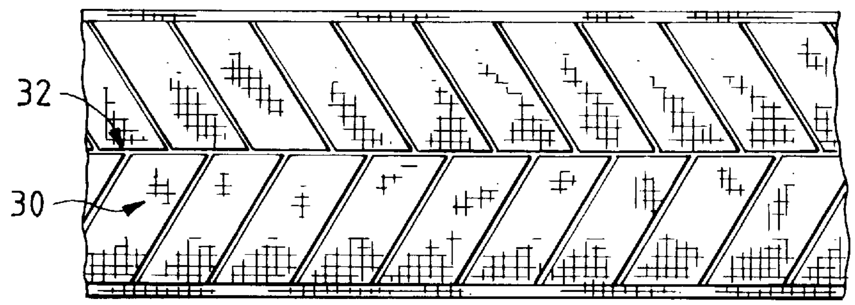
FIG. 6 is a second top view of the absorbent core of the present invention, together with additional optional layers.
Figure 7:
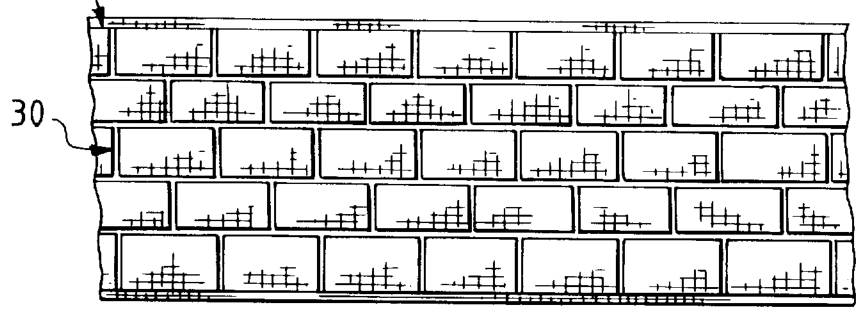
FIG. 7 is a third top view of the absorbent core of the present invention, together with additional optional layers.

The final product, in dry form, is shown in FIG. 2. Additional bonding patterns are shown in FIGS. 5–7. It will be seen that the product is a thin, patterned partial flat laminate having a plurality of flat unbonded zones 30 or individual pockets connected together by a plurality of intersecting indented thermal bond lines 32. The bond lines are uninterrupted except at the sealed margins and provide a continuous gridwork over the surface of the laminate. For the purpose of continuous production using rolls, the gridwork is a repeating pattern.

At the bond lines 32, some of the fibers of the adjacent fabric faces are at least partially fused together by the heat and pressure of the calender, and the surrounding fibers are densified relative to the surrounding fabric. The fabric is not completely fused along these lines, although the bond is permanent and will not delaminate during initial swelling of the pockets when exposed to liquid.

Although not preferred, it is possible in theory to form the bond lines 32 by application of intersecting lines of adhesive, such as a hot melt adhesive, or a curable adhesive to the inner surface of at least one of the layers 10 or 12, followed by joinder of the layers and heating.

The absorbent core is very thin and flexible in comparison with other types of cores and has a thickness of from less than about 7 mm and a dry basis weight of from about 80 to about 300 g per square meter. The SAP is capable of absorbing many times its weight of liquids.

Figure 3:
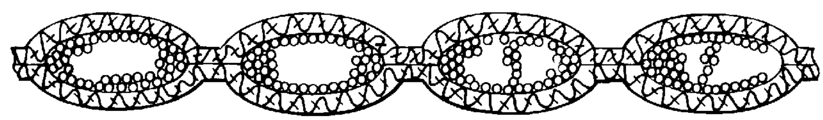
FIG. 3 is a sectional view of the core shown in FIG. 2 in a wet state.
Figure 4:
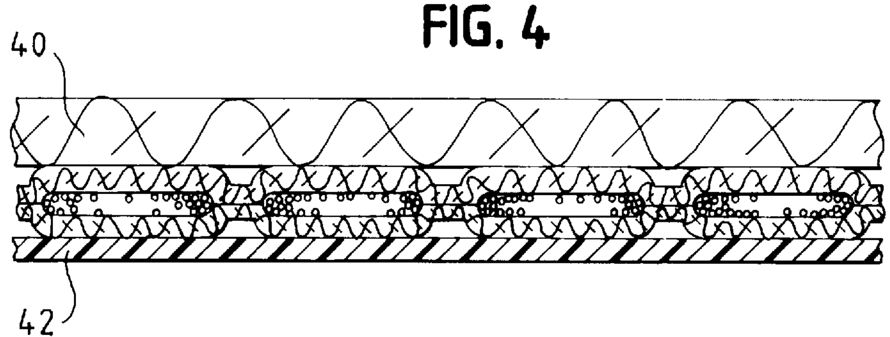
FIG. 4 is a schematic side view of the absorbent core of the present invention, together with additional optional layers.

When exposed to a stream of aqueous media in a confined location, the initial liquid is absorbed by the open areas in the grid, and excess liquid spreads out through the densified bonded lines to the remaining absorbent areas, as shown in FIG. 3. As liquid is absorbed, the SAP particles swell up and expand the open fabric layers in the form of connected pillows while the bond lines remain intact to define three dimensional flow channels and allow continued flow of liquid by capillary action or otherwise to adjacent pockets. Thus, absorption in one cell has no effect or possible blockage of absorption in other cells, and the rate of absorption and overall absorption capacity is greatly improved. The layers 10 and 12 are sufficiently strong to prevent any through penetration by the swollen SAP.

It may be seen in FIG. 3 that when the core is wet, the bond lines 32 are more pronounced furrows in comparison to the dry product and provide flow paths for excess liquids, either by wicking or by laminar flow. The depth of these lines is also increased if the core is wrapped around a curved portion of the body, as in the case of a diaper.

The swelling of the pockets in close relation to the body is also beneficial, in that the diaper or other garment tends to conform more closely to the body and prevent leaks.

While the heat seal lines 32 remain intact during initial swelling of the pockets, it is contemplated in some applications that forced generated by the swollen SAP particles near saturation can or will cause disruption of at least a portion of a seal line, thus providing additional volume capacity and transfer into adjacent pockets.

The speed of acquisition of liquid into the absorbent core can be enhanced by the use of an additional layer of a low density nonwoven fabric 40 (FIG. 2), which is applied against the porous outer layer 10 of the core. One type of suitable fabric is a 20–50 grams per square meter of through air bonded web of bicomponent fibers of 6–12 denier.

The present invention contemplates the use of various types of nonwoven liquid acquisition layers or structures, i.e., the layers or structures which face the source of liquid and transfer the liquid to the SAP in the core. Thus, the layer 10 may itself comprise a plurality of different types or layers of nonwoven webs, or, for example, may comprise bonded layers of different sizes of fibers, such as an outer layer of fine fibers bonded to an inner layer of fibers which are coarser or more hydrophilic than the outer layer, in order to enhance liquid transfer and distribution, or to provide a void volume to contain initial surges of liquid.

In addition, if the lower layer 12 of the core does not contain an impervious film, a separate outer film 42 may be provided on the lower outer layer 12 to prevent escape of liquid.

The absorptive core of the present invention may be used in the form as presently described. For example, it may be applied by strips of adhesive to underwear. Also, the core may be part of an assembly such as a diaper or other device used to absorb body fluids.

In comparison to conventional cores used in present day diapers containing wood pulp, the core of the present invention is clearly superior. The liquid absorption rate is up to fifty percent faster. Also, up to ninety percent of the SAP has absorbed liquid at saturation, compared to about fifty percent of cores based on wood pulp. Products such as disposable diapers containing the present core have very low bulk, allowing for more convenient and less expensive packaging, storage space and transport.

We claim:

1. A core for the absorption of liquids, said core consisting essentially of a pair of outer flat nonwoven porous fabric layers of thermoplastic fibers, each of said layers having a dry basis weight of from about 17.5 to 25 grams per square meter, said outer flat layers being heat sealed together along a plurality of intersecting lines to define a plurality of flat, closed, porous pockets, with said intersecting seal lines defining flow channels between pockets, and between 45 to 250 grams per square meter of liquid superabsorbing polymer in dry particulate form loosely contained in said closed pockets, said superabsorbing polymer being of the type in which the particles swell and remain as individual particles upon exposure to liquid, said core having a thickness of less than 7 mm in dry form, the contained superabsorbing polymer, after being exposed to liquid passing through said porous layers, swelling substantially to swell said pockets with said core defining a three dimensional bubble-like structure.

2. The core of claim 1 wherein said core comprises opposed parallel edges, and said intersecting seal lines comprise lines extending parallel to said edges.

3. The core of claim 1 wherein said outer layers comprise nonwoven fabric of polypropylene fibers.

4. A core for the absorption of liquids, said core consisting essentially of a pair of superimposed outer flat containment layers of thermoplastic materials, each of said outer containment layers having a dry basis weight of from about 17.5 to 25 grams per square meter and at least one outer containment layer being a porous nonwoven fabric comprising thermoplastic layers, a continuous intersecting gridwork of heat bond lines formed between said outer containment layers and defining a plurality of individual closed pockets in dry form, and between 45 to 250 grams per square meter of superabsorbing polymer particles loosely contained in said pockets, said pockets being free of cellulose pulp, the thickness of said the core in the dry condition being less than 7 mm and having a total basis weight of 80 to 300 grams per square meter said supersabsorbing polymer, when exposed to liquid, swelling to cause said pockets to enlarge and form a three dimensional bubble-like structure.

5. An absorbent structure core consisting essentially of a pair of flat layers, each of said layers having a dry basis weight of about 17.5 to 25 grams per square meter and at least one of said layers being porous to transfer of liquids, a plurality of permanent bonds between said layers defining a plurality of closed flat pockets and a plurality of permanent intersecting flow channels between said pockets, from about 45 to about 250 gsm of particles of a superabsorbing polymer disposed in said flat pockets, said core having a thickness of less than 7 mm on a dry basis and a total basis weight of from about 80 to about 300 gsm.

6. A combination including a core for the absorption of liquids and an acquisition layer, said core consisting essentially of a pair of outer flat nonwoven porous fabric layers of thermoplastic fibers, each of said layers having a dry basis weight of from about 17.5 to 25 grams per square meter, said outer flat layers being heat sealed together along a plurality of intersecting lines to define a plurality of flat, closed, porous pockets, with said intersecting seal lines defining flow channels between pockets, and between 45 to 250 grams per square meter of liquid superabsorbing polymer in dry particulate form loosely contained in said closed pockets, said superabsorbing polymer being of the type in which the particles swell and remain as individual particles upon exposure to liquid, said core having a thickness of less than 7 mm in dry form, the contained superabsorbing polymer, after being exposed to liquid passing through said porous layers, swelling substantially to swell said pockets with said core defining a three dimensional bubble-like structure, said core being in combination with said acquisition layer comprising a lower density nonwoven fabric layer in contact with one of said layers of nonwoven thermoplastic fibers for improving distribution of said liquid to said core.

* * * * *